(12) United States Patent
Schmitz et al.

(10) Patent No.: US 8,287,819 B2
(45) Date of Patent: Oct. 16, 2012

(54) DEVICE FOR SYNTHESIS OF RADIOPHARMACEUTICAL PRODUCTS

(75) Inventors: Fèdèric Schmitz, Fallais (BE); Pierre-Emmanuel Boeyen, Corroy-le-Chateau (BE); Vincent Tadino, Donceel (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 1505 days.

(21) Appl. No.: 10/450,308

(22) PCT Filed: Dec. 12, 2001

(86) PCT No.: PCT/BE01/00212
§ 371 (c)(1),
(2), (4) Date: Jun. 10, 2003

(87) PCT Pub. No.: WO02/051447
PCT Pub. Date: Jul. 4, 2002

(65) Prior Publication Data
US 2004/0028573 A1 Feb. 12, 2004

(30) Foreign Application Priority Data
Dec. 22, 2000 (EP) .................................... 00870323

(51) Int. Cl.
*B01L 3/00* (2006.01)
*B01L 99/00* (2010.01)
*F04B 19/00* (2006.01)
*B42F 13/00* (2006.01)
*B65D 75/00* (2006.01)

(52) U.S. Cl. ........ 422/501; 422/159; 422/430; 422/500; 422/504; 248/326; 248/335; 206/167

(58) Field of Classification Search .................. 422/104, 422/61, 102; 206/161, 167; 248/326, 335
See application file for complete search history.

(56) References Cited

U.S. PATENT DOCUMENTS
4,733,850 A * 3/1988 Thompson ................. 254/134.4
(Continued)

FOREIGN PATENT DOCUMENTS
WO WO 93/11871 6/1993

OTHER PUBLICATIONS
Charly et al. "A large scale manual production of [F]FDG using a synthetic unit made of sterile disposable components and operated by a master slave manipulator". *Appl. Radiot. Isot.*, vol. 41, No. 1, pp. 29-34 (1990).

*Primary Examiner* — Neil N Turk
(74) *Attorney, Agent, or Firm* — Fitch, Even, Tabin & Flannery, LLP

(57) ABSTRACT

The invention concerns a device for synthesis of radiopharmaceutical products based on chemical reagents contained in bottles, said device comprising several reaction compartments, transfer means between said bottles and said reaction compartments as well as mechanical means acting on said transfer means and enabling to monitor and control mechanically the transfer of chemical reagents. The invention is characterized in that it comprises: a fixed module including at least the mechanical means; a removable and disposable module, essentially in the shape of a support, whereon are arranged the transfer means between said bottles and said reaction compartments, said removable and disposable module not including any mechanical means; and means for securing said removable and disposable module to said fixed module.

1 Claim, 5 Drawing Sheets

U.S. PATENT DOCUMENTS

| | | |
|---|---|---|
| 5,312,592 A | 5/1994 | Andersson |
| 5,380,665 A * | 1/1995 | Cusack et al. ............... 436/53 |
| 5,415,843 A | 5/1995 | Andersson |
| 5,536,945 A * | 7/1996 | Reich .................... 250/507.1 |
| 5,759,513 A | 6/1998 | Nakazawa |
| 6,572,823 B1 * | 6/2003 | Donahue et al. ............ 422/63 |

* cited by examiner

DEVICE FOR SYNTHESIS OF RADIOPHARMACEUTICAL PRODUCTS

SUBJECT MATTER OF THE INVENTION

The present invention relates to a novel device for synthesis of radiopharmaceutical products from radioactive compounds.

The present invention relates more especially to the use of this device for synthesis of radiopharmaceutical products from reagents containing radioactive elements with a short half-life, such as $^{11}C$, $^{13}N$, $^{15}O$ or $^{18}F$.

PRIOR ART

In diagnostic applications, such as Positron Emission Tomography (PET), use is made of radiochemical compounds, also called radiopharmaceutical compounds, which are labelled by means of an element such as $^{11}C$, $^{13}N$, $^{15}O$ or $^{18}F$. One example of such compounds is 2-[$^{18}F$]fluoro-2-deoxy-D-glucose, commonly called $^{18}FDG$.

Synthesis of these radiopharmaceutical compounds with a short half-life is performed in apparatuses that enable the different chemical compounds for carrying out the synthesis to be brought into contact and heated during the reaction and allow the products obtained to be purified.

To avoid any risk associated with the handling of radioactive substances, these apparatuses are placed in a shielded and monitored environment. These apparatuses are generally linked to an automaton which commands the various operations enabling the performance of this synthesis, comprising reaction and heating stages, which are associated with transfers of chemical reagents.

Owing to the short half-life of these radioisotopes that are used, it is necessary to perform this type of synthesis at regular intervals. This multiplies the risks of contamination from one synthesis to another, while the end product is intended for injection into patients.

Moreover, a certain number of materials contained in the components of the synthesis apparatus are particularly sensitive to radioactivity and/or to chemical corrosion. This is the case, for example, with the valves or tubes allowing transfers to take place.

It is therefore necessary to wash and sterilise each component of the synthesis apparatus at regular intervals, especially all the tubing and all the valves which allow transfer of the reagents, hence the need to use components that can be sterilised easily. Users must furthermore ensure thorough, careful and regular maintenance of all the components of the apparatus.

U.S. Pat. No. 5,759,513 discloses an apparatus and a process for preparing radiochemical compounds in which, with the exception of the reagent labelled by means of an element with a short half-life, the reagents required are metered into containers beforehand. This gives a kit containing the said containers, the reactors, the columns and the transfer tubes fitted with valves, which are required for the process. This kit comprises a large number of elements, including valves. The overall cost does not allow it to be used as a single-use kit.

WO-A-93/11871 discloses an apparatus for preparing radiochemical compounds, comprising a single-use module. This apparatus is intended to be connected to reagent containers and comprises means of metering these reagents constituted by injectors provided with pistons and actuated by stepping motors. Complex, expensive means that require handling by the operator are necessary to connect the stepping motors to the rods of the injectors.

U.S. Pat. No. 5,415,843 describes an apparatus for manufacturing radiopharmaceutical compounds which has certain characteristics in common with that described in WO-A-93/11871. This apparatus includes a single-use disposable kit which comprises a plate and receptacles but not the connection tubes between the various receptacles.

U.S. Pat. No. 5,312,592 also describes an apparatus which has certain characteristics in common with that described in WO-A-93/11871. This document relates more especially to a disposable kit that can be used in the said apparatus and comprises a plate provided with openings and sleeves to support liquid injectors and to connect transfer tubes, as well as a hydrolysis receptacle.

The article by Chaly T. et al., Appl. Radiat. Isot. Vol. 41, No. 1, pp 29-34 (1990) in Int. J. "Radiat. Appl. Instrum. Part A" (Pergamon Press) describes a process for producing $^{18}FDG$ by using a synthesis unit comprising disposable sterile elements such as syringes, needles, tubes, adapters and stop valves.

OBJECTS OF THE INVENTION

It is an object of the present invention to provide a device for synthesis of radioactive products, in particular radiopharmaceutical products, from radioactive elements with a short half-life, which can be used easily.

In particular, it is an object of the present invention to provide a device which minimises the risks of contamination from one synthesis to another.

It is likewise an object of the present invention to provide a device which is easier to maintain and service.

In particular, it is an object of the present invention to provide a device which can be washed easily and sterilised easily.

BRIEF DESCRIPTION OF THE INVENTION

The present invention relates to a device for synthesis of radiopharmaceutical products from chemical reagents contained in bottles, the said device comprising several reaction compartments, transfer means between the said bottles and the said reaction compartments as well as mechanical means acting on the said transfer means and enabling to monitor and control mechanically the transfer of the chemical reagents, characterised in that it comprises:
  a fixed module including at least the mechanical means,
  a removable and disposable module, essentially in the shape of a support plate, on which the transfer means between the said bottles and the said reaction compartments are arranged, the said disposable and removable module not including any mechanical means, and
  means for securing the said removable and disposable module to the said fixed module.

The said disposable module preferably furthermore comprises the said bottles and the said reaction compartments.

The bottles are preferably pre-metered bottles.

The support plate preferably comprises means for the precise positioning of the transfer means.

The positioning means are preferably constituted by grooves in which the transfer means are placed.

The transfer means are preferably flexible tubes, the mechanical means are pistons, the transfer means, the mechanical means and the positioning means being capable of co-operating so as to form valves.

The securing means preferably comprise at least one opening, shoulders and fasteners.

The said shoulders are preferably located on the support plate, preferably at the four corners of the support plate, and are capable of fitting into fasteners located on the fixed module.

The said opening is preferably likewise located on the support plate, preferably at the centre of the said plate, and is capable of fitting into a fastener located on the fixed module.

The nature of the support plate (5) and that of the transfer means are preferably such that they allow washing of the said disposable module by steam autoclaving and/or its sterilisation.

The support plate is preferably made of ABS and the transfer means are preferably made of silicone.

The device preferably includes means of actuating the mechanical means of the fixed module.

The actuating means are preferably constituted by an automaton co-operating with a computer and forming part of the fixed module.

The present invention likewise relates to a disposable and removable module intended for association with a fixed module by securing means and essentially in the form of a support plate comprising means for positioning the means for transferring chemical reagents.

The said module preferably furthermore comprises bottles and reaction compartments.

The said module preferably likewise comprises columns.

The positioning means are preferably constituted by grooves capable of receiving transfer means.

The present invention likewise relates to a process for synthesising radiopharmaceutical products using the device according to the present invention and comprising the following stages:

the transfer means are arranged on the support plate,
the bottles containing the chemical reagents are fixed to one of the ends of the transfer tubes,
the said support plate with the transfer means is attached to the fixed module with the aid of securing means,
the transfer means are connected to the various elements of the fixed module,
the various operations required for synthesis of the pharmaceutical products, including the actuation of the mechanical means, are commanded via the automaton.

Before commanding the various operations required for synthesis of the pharmaceutical products, a test to verify the tightness of the device is preferably carried out via the automaton.

The present invention also relates to the use of the device according to the present invention or of the module according to the present invention for synthesising radiopharmaceutical compounds containing radio-elements with a short half-life, preferably $^{11}C$, $^{13}N$, $^{15}O$ or $^{18}F$.

DETAILED DESCRIPTION OF A PREFERRED EMBODIMENT OF THE INVENTION

It should be noted that the figures presented here relate to a device intended for synthesising $^{18}FDG$. These figures are given purely by way of example to illustrate the invention, but they do not in any way limit its scope. The person skilled in the art will easily be able to adapt the various elements of the device depending on the type of synthesis to be performed.

Figure 1:
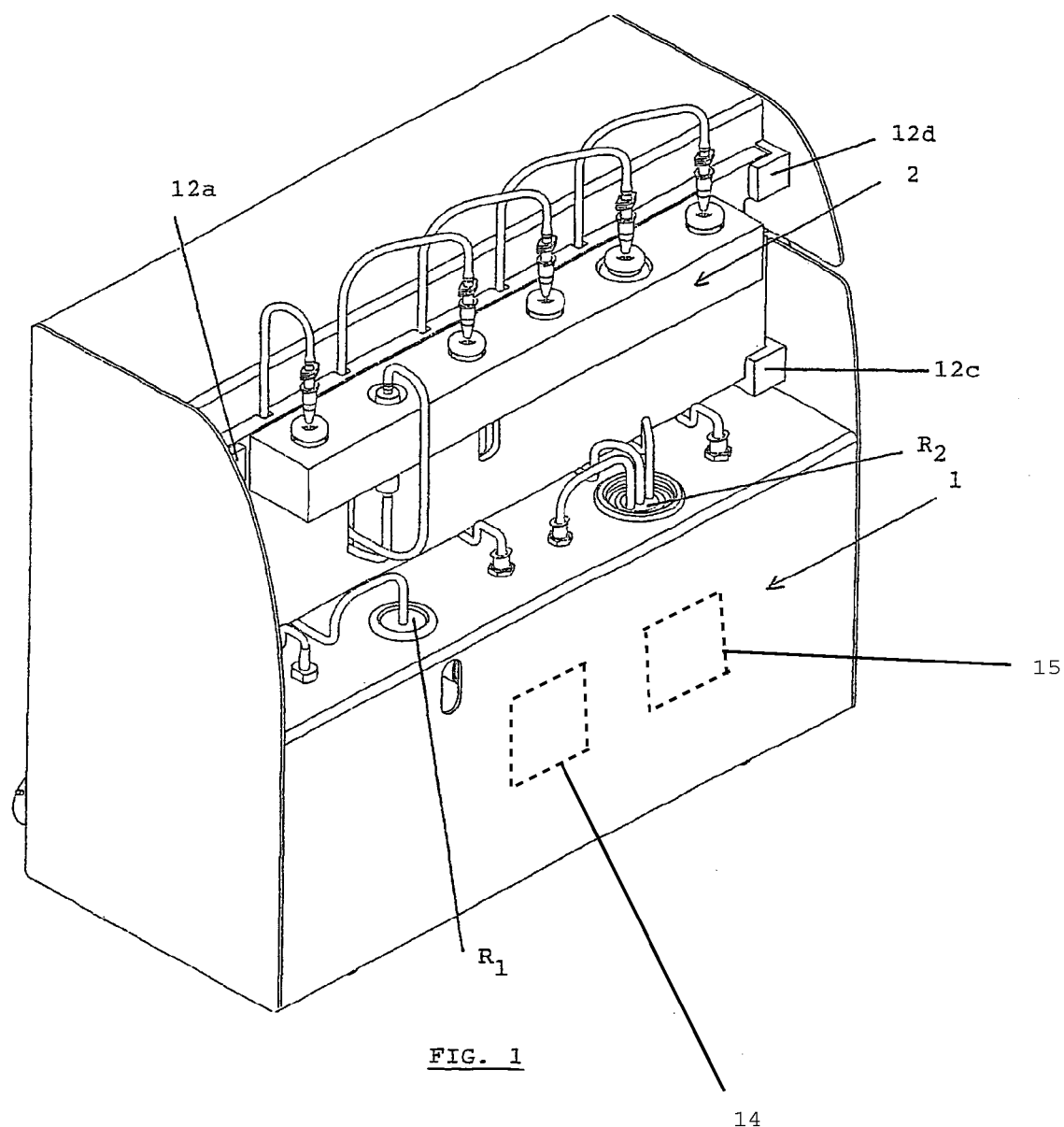
FIG. 1 provides a general view of the disposable module fixed on the fixed module of the device according to the present invention.

As illustrated in FIG. 1, the device according to the present invention comprises a fixed module 1 and a removable and disposable single-use module 2. When the device is in operation, the removable and disposable module 2 is fixed on the fixed module 1.

Figure 2:
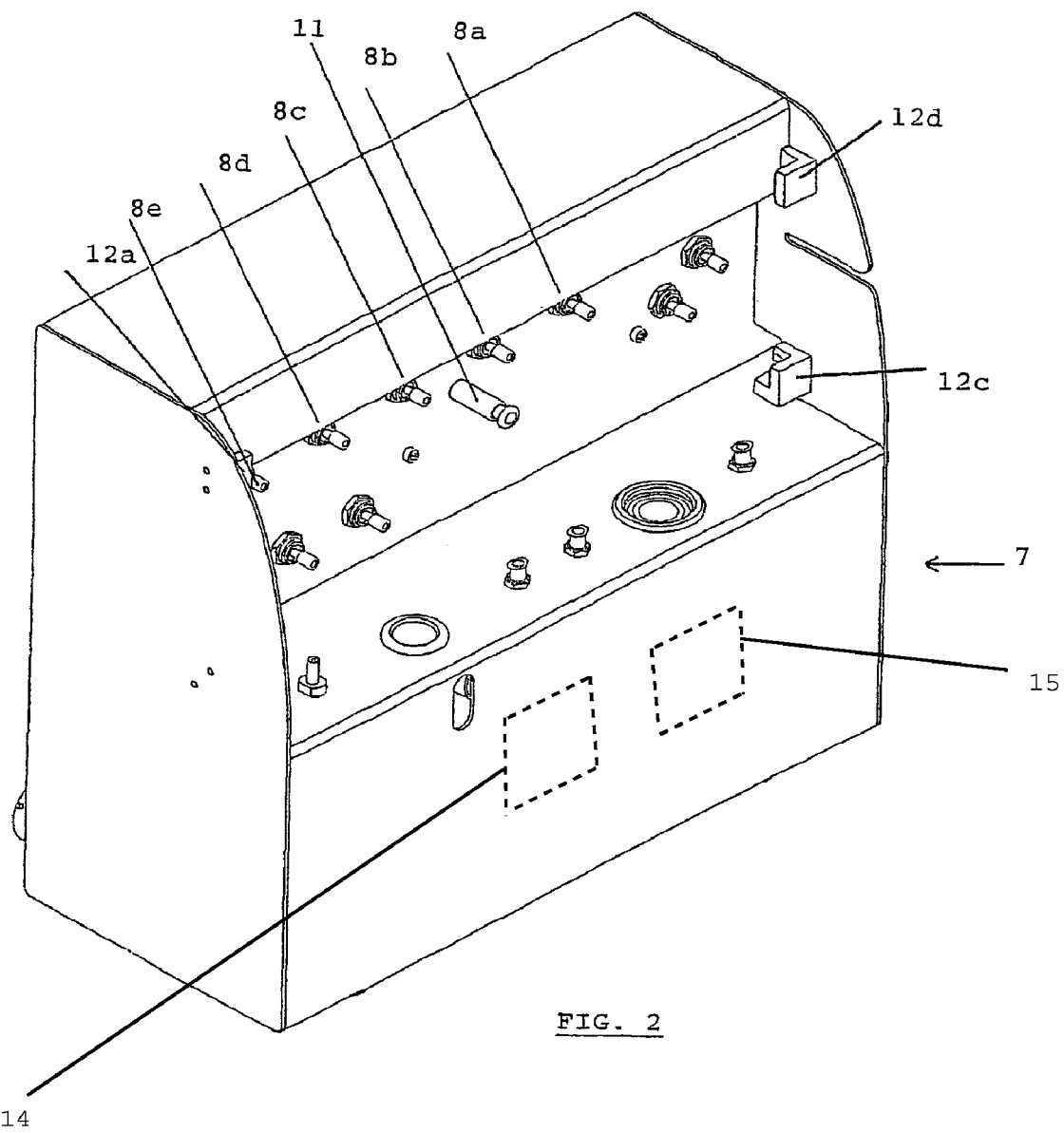
FIG. 2 represents a perspective view of the fixed module in the device according to the present invention.

FIG. 2 provides a detailed view of the fixed module. The fixed module 1 is here in the form of a case 7, on which pistons 8a, 8b, 8c, 8e, . . . are arranged.

The module 1 likewise comprises an automaton 14 controlled by a computer 15 although these are not shown here. The automaton controls all the operations required to implement synthesis of the radiopharmaceutical products, in particular the movement of the pistons 8a, 8b, 8c, 8d, 8e, . . . .

Moreover, to enable the device to be used, the module 1 comprises securing means which enable it to be fixed to the disposable module 2. These securing means can take the form of fasteners arranged according to a precise configuration. In the case shown in FIG. 2, these fasteners are of two types. There are, on the one hand, the four fasteners 12a, 12b, 12c and 12d and the central fastener 11, the said central fastener 11 here being in the form of a stud. The presence of the central fastener 11 is intended for securing the fixing of the module 2 to the module 1. It furthermore allows the pressure exerted by the pistons 8a, 8b, 8c, 8d, 8e, . . . to be counteracted.

Figure 3:
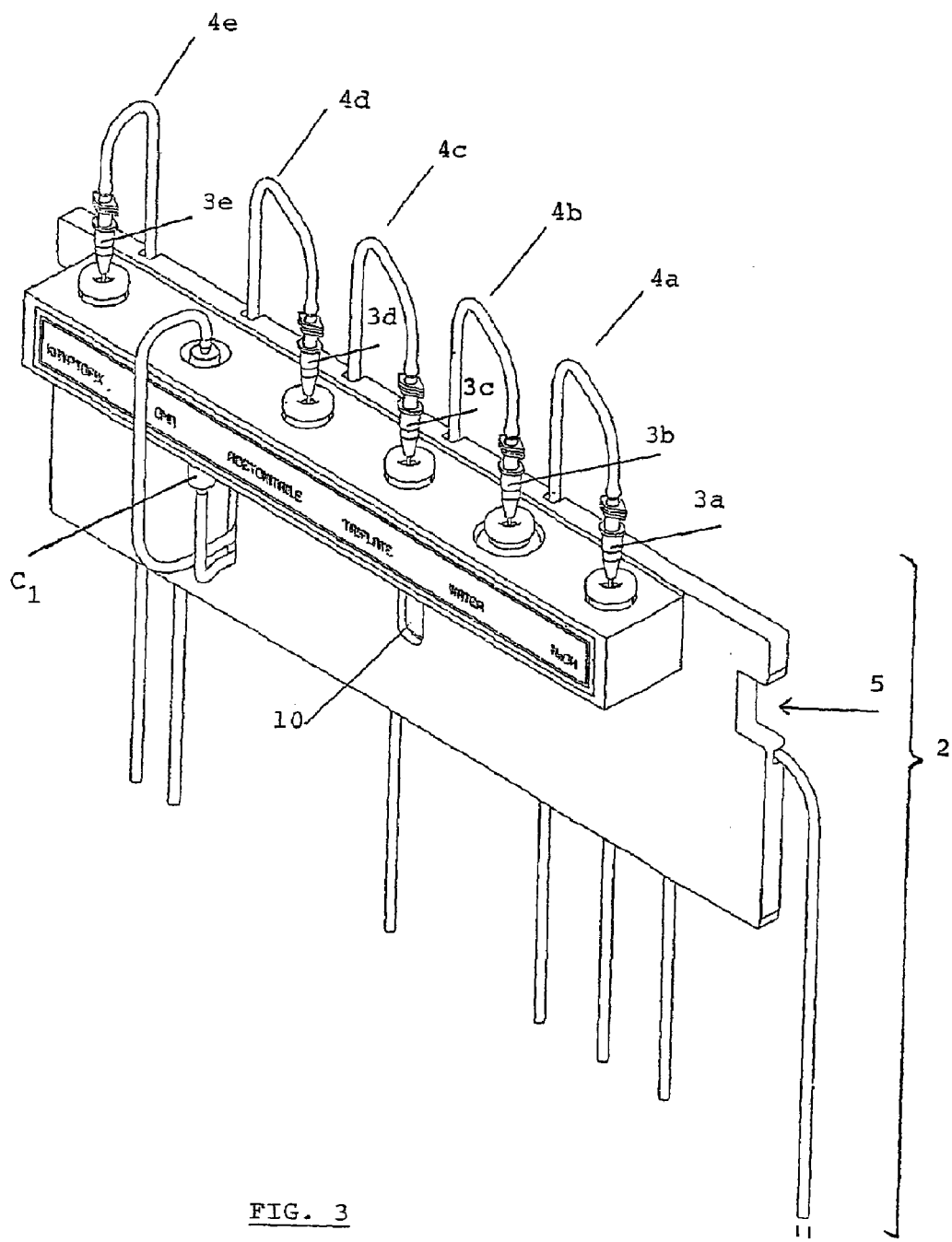
FIG. 3 represents a perspective view of the front face of the disposable module without the fixed module in the device according to the present invention.
Figure 4:
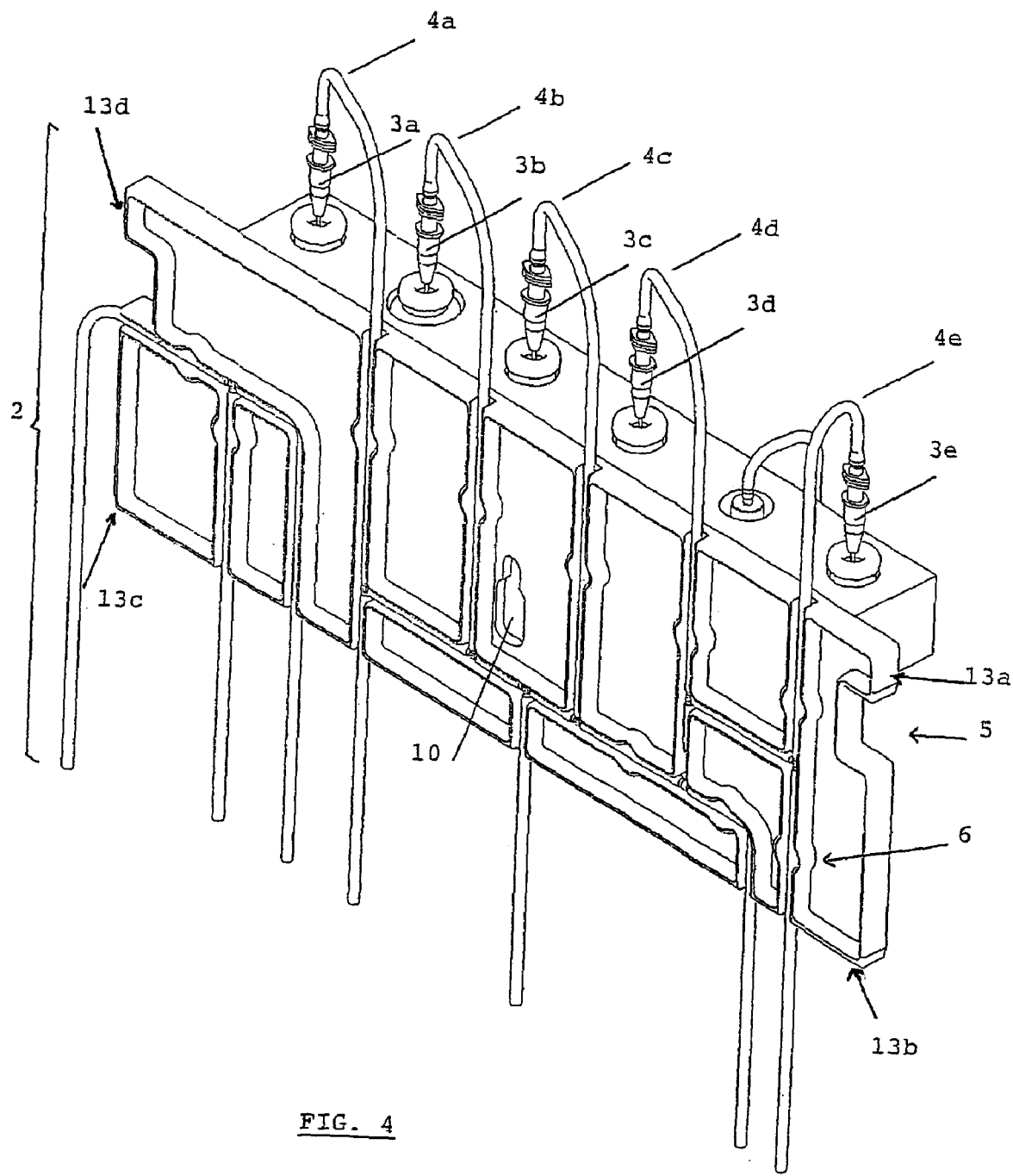
FIG. 4 represents a perspective view of the rear face of the disposable module without the fixed module in the device according to the present invention.

FIGS. 3 and 4 give a more detailed view of the various elements of the disposable module according to the present invention. The disposable module 2 comprises at least:

one plate 5, in which a network of grooves 6 is formed according to a precise configuration;
five bottles 3a, 3b, 3c, 3d,3e containing the pre-metered chemical reagents,. respectively Kryptofix, $K_2CO_3$, acetonitrile, triflate, water and sodium hydroxide;
tubes 4a, 4b, 4c, 4d, 4e, . . . for circulating the chemical products within the synthesis device, these tubes being flexible in the present case, and one of their ends being connected to the bottles 3a, 3b, 3c, 3d, 3e, respectively,
columns, including outlet columns (not shown). The module 1 here comprises at least four columns, column $C_1$ as shown in FIG. 3 and columns $C_2$, $C_3$, $C_4$, not shown,
reaction compartments $R_1$ and $R_2$, as shown in FIG. 1.

The said plate 5 has a dual function. Its first function is that the plate 5 serves as a support for the tubes 4a, 4b, 4c, 4d, 4e when these tubes are fixed in the grooves 6. The configuration of these grooves 6 allows very accurate positioning of the tubes 4a, 4b, 4c, 4d, 4e relative to one another. In other words, the tubes 4a-4e, the pistons 8a-8e and the grooves 6 are capable of co-operating so as to form valves. The pistons 8a-8e associated with the portion of the tubes 4a-4e which face them thus form valves of the "pinch-valve" type, that is to say piston valves.

It is thus important that the tubes should be positioned correctly to enable these valves to operate correctly. In particular, the pistons 8a-8e should be able to act precisely on the said tubes 4a-4e.

The second function of the plate 5 is to serve as an interface between the fixed module 1 and the disposable module 2. The plate 5 is provided with securing means which enable the said disposable module 2 to be fixed on the said fixed module 1. By virtue of their shape, these securing means located on the disposable module 2 are complementary to the securing means located on the fixed module 1.

According to the exemplary embodiment shown in FIGS. 3 and 4, these securing means on the one hand take the form of shoulders 13a, 13b, 13c, 13d, each located at one corner of the plate 5. These shoulders 13a, 13b, 13c, 13d are capable of fitting into the respective fasteners 12a, 12b, 12c, 12d. On the other hand, the securing means take the form of an opening 10 which is located in the centre of the plate 5 and into which the central fastener 11 of the fixed module 1 can fit. By virtue of its central position in the plate 5, the opening 10 makes it possible to ensure that the disposable module 2 is secured in an optimum manner to the fixed module 1 while the device is being used.

However, the securing means can take other forms.

Figure 5:
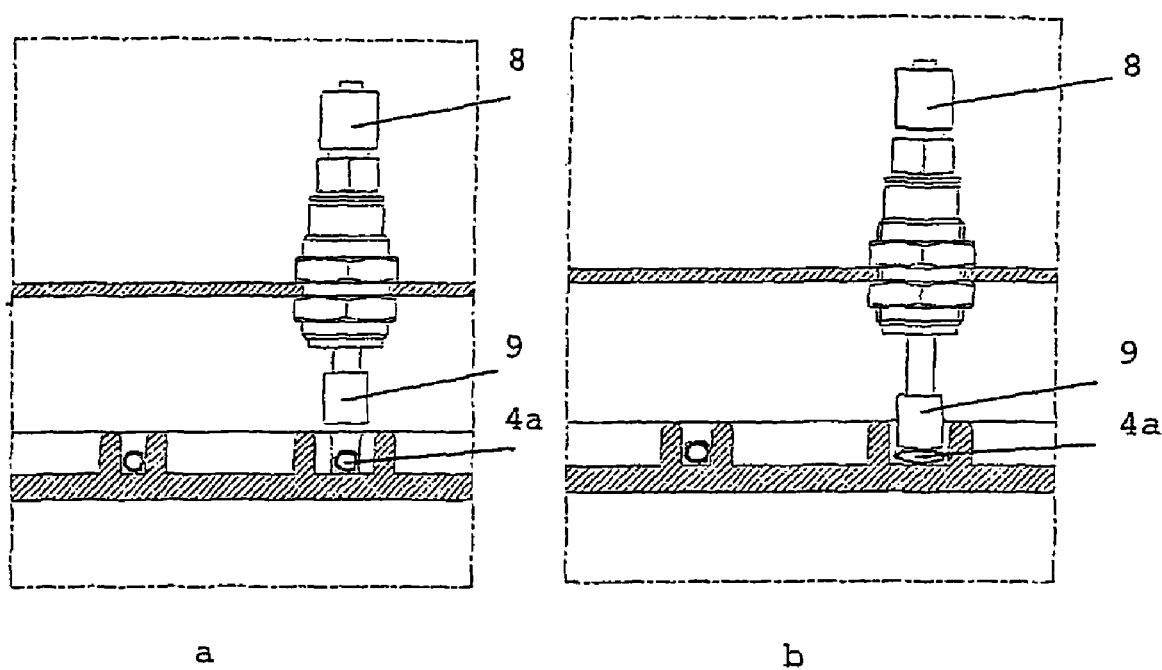
FIG. 5 shows the mechanism for closing the flexible tubes belonging to the disposable module by means of pistons belonging to the fixed module according to a preferred embodiment of the invention.

FIG. 5 illustrates how the pistons 8a-8e located on the fixed module 1 bring about either the opening or closure of the tubes 4a-4e of the disposable module 2 as a function of the movement that they are commanded to make by the automaton. In view a, this figure shows the head 9 of one of these pistons 8a and a section of one of the flexible tubes 4a in an open position, that is to say when the tube 4a is open. In this position, the head 9 of the piston 8a is disengaged from the tube 4a and transfers of chemical products are then allowed. When commanded by the automaton, on the other hand, the head 9 of the piston 8a is displaced and comes to exert a pressure on the section of the tube 4a, as illustrated in view b, and the tube 4a is then closed, preventing any transfer of chemical products.

In relation to the prior-art devices, the present invention has the original characteristic of being without any mechanical means, in particular mechanical means of opening and closing the tubes, these mechanical means being located on the fixed module 1.

By virtue of this fact, the module 2 can be attached and removed easily. It can be fixed easily on the fixed module 1. Such a module 2 likewise has the advantage of being inexpensive, owing especially to the absence of mechanical means in this module, and, by virtue of this fact, allows single use.

According to a preferred embodiment, the plate 5 is made of ABS and the tubes 4a, 4b, 4c, 4d, 4e, . . . are made of silicone. The advantage of such a choice in terms of the materials used is that these elements are capable of withstanding the high pressures, in particular the pressures exerted by the pistons, during the use of the device. It likewise makes it possible to limit the waste resulting from incineration of used disposable modules.

Insofar as their composition allows, the various elements constituting this module can be sterilised easily, in particular by the conventional techniques such as sterilisation by gamma radiation.

The example described below is an example of the use of the device according to the present invention for synthesis of $^{18}$FDG. However, this example is given only by way of illustration. Other uses are possible.

To synthesise $^{18}$FDG with the device according to the present invention, $^{18}$F$^-$ is first of all extracted from the mixture $H_2^{18}O$—$H_2O$—$^{18}F^-$. To do this, the mixture is transferred by means of gaseous helium as far as the column $C_1$ containing an anion exchange resin, such as QMA Waters™. Column $C_1$ allows recovery of the $^{18}F^-$, while $H_2^{18}O$—$H_2O$ is transferred to the reaction compartment R1.

Tube 4e is opened to allow 0.75 ml of a solution of $K_2CO_3$/K2.2.2/$H_2O$/$CH_3CN$ contained in bottle 3e to be transferred through column C1 with the aid of a vacuum pump 16 in a reaction compartment or reactor $R_2$. The $^{18}F$— is thus eluted, and it is transferred to reaction compartment $R_2$.

The temperature of the reactor $R_2$ is increased to 90° C. and $H_2O$ is eliminated by forming an azeotrope with acetonitrile.

Tube 4d is then opened, and 0.5 ml of acetonitrile contained in bottle 3d is then transferred with the aid of a vacuum pump 16 in reaction compartment R2.

The traces of $H_2O$ are eliminated by forming an azeotrope with acetonitrile. The evaporation is continued to complete the drying.

Tube 4c is opened so as to transfer with the aid of a vacuum pump 16 a solution of 13 mg of 1,3,4,6-tetra-O-acetyl-2-O-trifluoromethane-sulphony-1-β-D-mannopyranose in 1 ml of acetonitrile contained in bottle 3c into compartment $R_2$. The temperature of the said compartment $R_2$ is brought to 85° C.

The acetonitrile is then evaporated in vacuo while maintaining the temperature in the reactor $R_2$ between 90 and 85° C.

Tube 4b is then opened so as to transfer 1 ml of $H_2O$ contained in bottle 3b with the aid of a vacuum pump 16. The reactor $R_2$ is then cooled.

Tube 4a is then opened so as to transfer 1 ml of a solution of 0.5 N NaOH contained in bottle 3a to reactor $R_2$ with the aid of a vacuum pump 16.

Nitrogen at a pressure of 400 mbar is used to transfer the contents of reactor $R_2$ through purification columns $C_2$, $C_3$, $C_4$ (not shown) arranged in series at the outlet of the circuit.

Tube 4b is opened for a second time to transfer 4 ml of $H_2O$ from bottle 3b to reactor $R_2$ with the aid of a vacuum pump 16.

Nitrogen at a pressure of 400 mbar is used a second time to transfer the contents of reactor $R_2$ through purification columns $C_2$, $C_3$, $C_4$.

Finally, it will be noted that the device according to the present invention offers the advantage of being particularly compact, thus reducing the volume of the shielded chamber in which it is used and hence the quantity of lead.

The invention claimed is:

1. A device which synthesizes radiopharmaceutical products from chemical reagents, the device comprising:
   a fixed module which includes pinch valves;
   a disposable module; and
   a mounting device which removably secures the disposable module to the fixed module, the disposable module comprising:
   a support plate having grooves, the grooves having widened areas;
   bottles configured to contain and provide pre-metered amounts of the chemical reagents;
   one or more reaction compartments located in the disposable module; and
   flexible tubes configured to deliver the chemical reagents from the bottles to the one or more reaction compartments, wherein the tubes in the disposable module are positioned in the grooves on the support plate in the disposable module and the support plate is configured to position the tubes adjacent the pinch valves in the fixed module and which pinch valves pinch the tubes to control the flow of the chemical reagents from the bottles in the disposable module to the one or more reaction compartments in the disposable module to provide the radiopharmaceutical products, the disposable module not including a mechanical device which controls the flow of chemical reagents through the tubes; and wherein the pinch valves in the fixed module comprise one or more pistons acting on the flexible tubes of the disposable module, the pistons configured to engage the flexible tubes and effect control of the transfer of the chemical reagents from the bottles of the disposable module, and wherein the pistons are located opposite the widened areas of the grooves to permit the flexible tubes to compress and the pistons and the tubes to co-operate to form valves.

* * * * *